United States Patent
Corwin et al.

(10) Patent No.: US 8,405,518 B2
(45) Date of Patent: Mar. 26, 2013

(54) UNIVERSAL PERSONAL EMERGENCY MEDICAL INFORMATION RETRIEVAL SYSTEM

(76) Inventors: Steven R. Corwin, Smyrna, GA (US); Laurie Wheeler-Snyder, Smyrna, GA (US)

(*) Notice: Subject to any disclaimer, the term of this patent is extended or adjusted under 35 U.S.C. 154(b) by 744 days.

(21) Appl. No.: 12/473,910

(22) Filed: May 28, 2009

(65) Prior Publication Data

US 2009/0295569 A1     Dec. 3, 2009

Related U.S. Application Data

(60) Provisional application No. 61/056,719, filed on May 28, 2008.

(51) Int. Cl.
*G01V 3/00* (2006.01)
(52) U.S. Cl. .................................................. 340/853.9
(58) Field of Classification Search ................ 340/853.9
See application file for complete search history.

(56) References Cited

U.S. PATENT DOCUMENTS

| | | | | |
|---|---|---|---|---|
| 2006/0187061 A1* | 8/2006 | Colby | .................. | 340/572.8 |
| 2006/0224420 A1* | 10/2006 | Willis | ...................... | 705/3 |
| 2007/0120683 A1* | 5/2007 | Flippen et al. | .......... | 340/572.8 |
| 2007/0200712 A1* | 8/2007 | Arneson et al. | .......... | 340/572.8 |
| 2007/0222599 A1* | 9/2007 | Coveley et al. | .......... | 340/572.4 |
| 2008/0215373 A1* | 9/2008 | D'Ambrosia | ................. | 705/3 |
| 2009/0008443 A1* | 1/2009 | Levovitz et al. | ............. | 235/380 |
| 2009/0160617 A1* | 6/2009 | Mullen et al. | ................ | 340/10.1 |
| 2009/0273455 A1* | 11/2009 | Sweeney et al. | ......... | 340/286.07 |

* cited by examiner

*Primary Examiner* — Rexford Barnie
*Assistant Examiner* — Dru Parries
(74) *Attorney, Agent, or Firm* — Ryan A. Schneider, Esq.; Troutman Sanders LLP

(57) ABSTRACT

A universal personal emergency medical information retrieval system, wherein information is written onto an RFID tag that is affixed to a carrier element, such as the back of the user's driver's license, passport, national identity card, school identification card, other form of identification, or cell phone. Medical personnel are alerted to the presence of the RFID tag by a universally accepted system identifier affixed to the carrier element, by scanning the patient with a handheld scanner, or by an RFID scanning portal. The emergency medical personnel can then download the user's information and identification photo using an RFID scanner. This information can then be used appropriately for proper emergency diagnosis and treatment. The RFID scanner can also be connected to a computer or computer network to retrieve additional information from a central database or to further disseminate the information contained on the RFID tag.

18 Claims, 7 Drawing Sheets

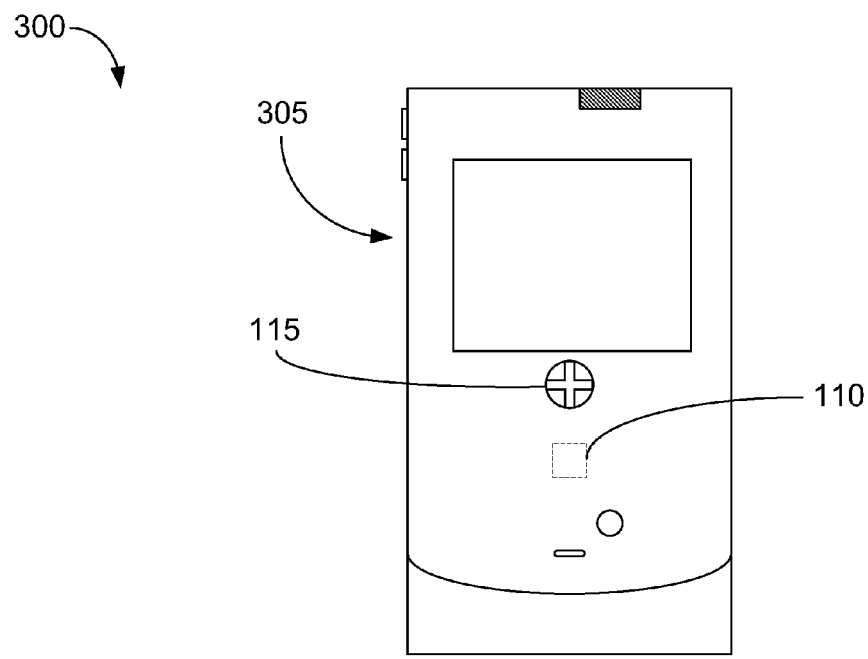
FIG. 3a
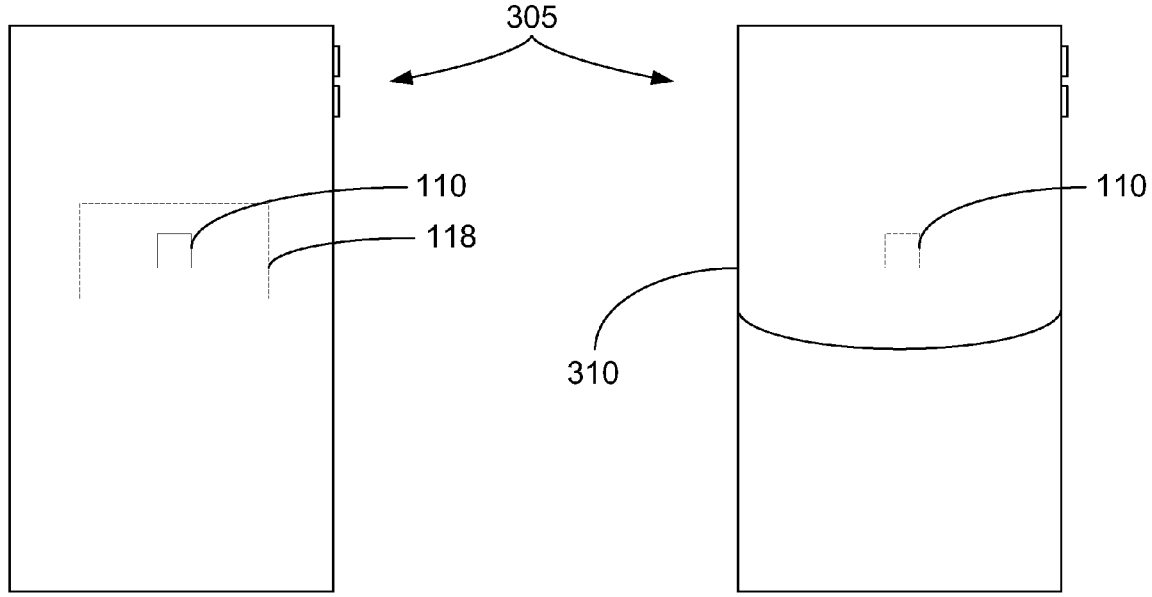
FIG. 3b
FIG. 3c

UNIVERSAL PERSONAL EMERGENCY MEDICAL INFORMATION RETRIEVAL SYSTEM

CROSS REFERENCE TO RELATED APPLICATION AND PRIORITY CLAIM

This application claims priority to, and the benefit of, U.S. Provisional Patent Application No. 61/056,719, filed 28 May 2008, said provisional patent application is incorporated herein by reference in its entirety as if fully set forth below.

BACKGROUND OF THE INVENTION

1. Field of the Invention

The present invention relates to a universal personal emergency medical information retrieval system and more particularly to a system wherein personal and medical information is written onto a passive, non-rewriteable radio frequency identification (RFID) tag using an RFID writer. It is to such a system that the present invention is primarily directed.

2. Description of Related Art

Emergency medical personnel are often confronted with a situation in which they need critical medical information about a patient, but are unable to obtain the information in a timely manner. This can be because the patient is unconscious, altered, does not speak the local language, or simply does not possess the information. Relevant medical information can include, among other things, blood type, Rh factor, current or past illnesses, current medications, allergies, and surgical history. Lack of information can result in suboptimal, delayed, or even deleterious treatment.

First responders, for example, often arrive on scene only to find one or more persons unconscious or badly injured. This can be as a result of, for example, a traffic accident, shooting, or natural disaster. First responders can need to give blood products to those with blood loss, and antibiotics or pain medication to those with injuries. Any of these treatments can be required simply to enable the injured party to survive transportation to the hospital. To any given patient, however, any or all of these treatments, if improperly administered, can be life threatening.

Another common scenario is that of children who are brought into the emergency room by a teacher, babysitter, or non-custodial parent. In this situation, neither the teacher nor the child may have the relevant medical information. If emergency personnel cannot reach the child's custodial parent or pediatrician in a timely manner, this can likewise cause improper or delayed treatment.

Elderly patients, patients with multiple medical conditions, or patients with diseases that are simply difficult to treat can be prescribed multiple medications. One example is the complex drug cocktail required to maintain low virus levels in patients infected with human immunodeficiency virus ("HIV"). When multiple drugs are used, the patient may not be able to remember all the drugs they take, much less possible drug interactions created thereby. This can create a situation in which medical personnel cannot effectively administer new drugs to the patient for fear of dangerous drug interactions with the patient's current regimen.

Patients are frequently forced to go to the hospital while traveling in foreign countries. This can be due to the local water or food conditions or merely due to happenstance. Additionally, many people never learn the native language for the country in which they live (e.g., immigrants or military personnel). Hospitals often have interpreters to cope with this situation, but cannot have an interpreter for every language they encounter, nor are interpreters generally available in ambulances or at the scene. Additionally, finding the interpreter needed and interpreting the patient's needs takes additional time. This can create a situation in which medical treatment is delayed due to a language barrier.

Patients in need of medical attention are often unconscious or altered due to, for example, injury, heart attack, stroke, drugs, alcohol, blood loss, low blood pressure, undiagnosed or untreated mental condition, low blood sugar, or dehydration. If the injured person has significant blood loss, for example, it can be necessary to give the person blood products in the field. Providing incorrectly matched blood, whether related to type, antibodies, or other factors, can result in illness and death due to, among other things, febrile non-hemolytic transfusion reactions, acute hemolytic reaction, or anaphylaxis. The use of O-negative blood can mitigate some, but not all, of the risks associated with blood transfusions. Properly matched blood type and antigens provide the best solution when blood transfusion is necessary.

Advancements in pharmacology have improved the length and quality of life for many. The resulting increase in the number of people using prescription and non-prescription drugs, however, can lead to a concomitant increase in dangerous drug allergies and drug interactions. Drug allergies can lead to, among other things, anaphylaxis, a severe whole body allergic reaction, that can be fatal in a matter of minutes if left untreated. Combining more than one drug, even over-the-counter drugs, can also cause severe, sometimes fatal, drug interactions. Combining Cialis®, a common erectile dysfunction drug, with nitrates, used to treat chest pain, for example, can cause abnormally low, even fatal, hypotension (low blood pressure).

Quick and accurate treatment can often spell the difference between a full recovery and lengthy hospital stays, permanent disability, or death. Proper treatment is desirable, not only for the obvious reason, i.e., the health of the patient, but also for the healthcare system as a whole. Improper treatment can result in complications that worsen patient outcome, increase length of hospital stay, and/or increase treatment and drug costs. This can increase the costs associated with the primary hospital visit and can also create, or increase, costs associated with, among other things, follow-up, and physical therapy.

Additionally, improper treatment can result in an increased number of malpractice and/or wrongful death suits against healthcare providers. The costs associated with higher malpractice insurance premiums and litigation are simply built into pricing and passed along to the end patient by healthcare and pharmaceutical providers. Ultimately, therefore, improper treatment results in an increase in treatment costs, medications costs, and costs associated with health insurance.

Systems currently in place to provide healthcare providers with critical medical information would best be described as primitive. Medic Alert® bracelets, for example, are very limited in the amount of information they can provide simply due to the space limitations of the bracelet. So, for example, the bracelet can simply provide "diabetes" as the medical condition, and include the patient's id number and a phone number to call for more information. Providers must then dial the number on the bracelet to obtain additional medical information, which can cause critical delays in treatment. Additionally, many patients do not wear the bracelets for, among other things, fashion reasons, medical reasons, or simply because they forget to wear it from time to time. Provided the patient wears the bracelet, the medical information contained thereon is usually too limited to assist in effective treatment.

Patients with more serious or extensive medical problems may elect to carry more complete personal medical records with them. However, the methods for doing so are extremely fragmented. The methods can include, but are not limited to, carrying their medical file in their pocket or handbag, carrying cards in their wallets with some of their medical information printed on them (available space on the card can be a limiting factor), a computer memory storage device such as a USB memory stick, smart card, or bar code with medical records saved thereon, or even an ID card or insurance card listing a website or phone number with which the treating healthcare provider can retrieve the patients medical information.

Alternatively sometimes patients will be with a friend or family member who can supply important medical information to the treating health care provider. This information is often incomplete or inaccurate, however, and can be of limited help. In many situations, incomplete or inaccurate information is relied upon to the patient's detriment.

The lack of uniformity, combined with time constraints often present in medical emergencies, often leads to this information remaining undiscovered. This can be because the emergency medical personnel do not know the patient has this information, in what form they have the information, or because they simply never find the information. Further, the medical provider can be required to have multiple readers to access disparate types of media storage devices, i.e. smart cards, USB keys, and bar codes. Alternatively, if an emergency patient has a card with a website or a phone number, the medical provider must then access an internet connection or phone to obtain the medical file, which can also cause delays.

What is needed therefore is a system that uses a single medical record storage device that enables medical personnel to have a single reader to access a patient's medical information. The system should be easy to implement and cost effective. The system should preferably be incorporated into an item that the patient already carries. The system should provide critical medical information to medical personnel using a simple and cost effective reader. It is to such a device that embodiments of the present invention are directed.

BRIEF SUMMARY OF THE INVENTION

Briefly described, in its preferred form, the present invention is an improved emergency medical information retrieval system. Personal emergency medical information can be written onto a passive, non-rewriteable RFID tag that is affixed to the back of the holder's driver's license, passport, national identity card, school identification card, or cell phone.

Emergency medical personnel can be alerted to the presence of this RFID tag by a universally accepted medical alert sticker affixed to the front of the identification card or by simply scanning the patient, their wallet, their handbag, or their cell phone with an RFID scanner. Medical personnel can then quickly and automatically download the stored medical information using a computer, where the essential medical information can be read and used appropriately for proper emergency diagnosis and treatment.

In some embodiments, the invention as currently claimed can be a universal personal emergency medical information retrieval system that includes a carrying element, a radio frequency identification (RFID) tag, detachably affixed to the carrying element, for storing emergency medical information, and a system identifier, detachably affixed to the carrying element, for indicating the presence of the emergency medical information retrieval system. In some embodiments, the carrying element can be a form of identification. In other embodiments, the carrying element can be a cell phone.

In some embodiments, the RFID tag can be a passive RFID tag. In some embodiments, the medical information stored on the RFID tag can be stored in a flexible database structure. In some embodiments, a handheld RFID scanner can be used to retrieve the medical information stored on the RFID tag. In some embodiments, the medical information stored on the RFID tag can be password protected, encrypted, or both. In still other embodiments, the medical information stored on the RFID tag can include a digital picture of the user to confirm the identity of the patient. In an alternative embodiment, the system can further comprise an RFID tag protector, disposed in an overlying manner to the RFID tag, to provide protection for the RFID tag against physical damage.

In other embodiments, the currently claimed invention is a universal personal emergency medical information retrieval system that can include a carrying case, such as a clear plastic sleeve, a radio frequency identification (RFID) tag, detachably affixed to the carrying case, for storing emergency medical information, a system identifier, detachably affixed to the carrying case, for indicating the presence of the universal personal emergency medical information retrieval system, and a central database for storing a user's medical information. In some embodiments, the central database is maintained by a central database hosting website. In other embodiments, emergency medical information can be one of a telephone number or a website address for accessing the medical information in the central database. In still other embodiments, all medical information can be stored on the RFID tag, obviating the need to access a central database via the internet or a hospital network computer.

In some embodiments, the central database is maintained locally in one of a hospital or a hospital network. In other embodiments, the system can also include a handheld RFID scanner for retrieving the medical information stored on the RFID tag. In some embodiments, the handheld RFID scanner can provide emergency medical information to a computer in a medical treatment facility over a network. In other embodiments, the computer can automatically access the central database to retrieve additional medical information.

In some embodiments, the invention, as currently claimed, can include a method for providing a universal personal emergency medical information retrieval system comprising marking the carrying element with a system identifier to alert medical personnel that the system is installed on the carrying element, writing the user's medical information to the RFID tag using an RFID tag writer, and detachably affixing the RFID tag to the carrying element. In some embodiments, the method can also include detachably affixing an RFID tag protector to the carrying element in an overlying manner to the RFID tag to protect the RFID tag. In some embodiments, the medical information can only be written to the RFID tag one time. In other embodiments, the medical information is written to the RFID using encryption, password protection, or both.

These and other objects, features and advantages of the present invention will become more apparent upon reading the following specification in conjunction with the accompanying drawing figure.

BRIEF DESCRIPTION OF THE FIGURES

FIG. 3a illustrates a front view of a cell phone with a universal personal emergency medical information retrieval system, in accordance with some embodiments of the present invention.

FIG. 3b illustrates a rear view of a cell phone with a universal personal emergency medical information retrieval system, in accordance with some embodiments of the present invention.

FIG. 3c illustrates a rear view of a cell phone with a universal personal emergency medical information retrieval system installed in the battery compartment of the phone, in accordance with some embodiments of the present invention.

DETAILED DESCRIPTION OF THE PREFERRED EMBODIMENTS

To facilitate an understanding of the principles and features of embodiments of the invention, they are explained hereinafter with reference to implementations in illustrative embodiments. Embodiments of the invention are described in the context of a medical record information system, and in particular, to a universal emergency personal medical information system. Additionally, embodiments of the invention relate to a method for providing such a system.

The present invention can provide immediate, critical medical information to medical personnel, which can be essential to saving the person's life. Additionally, the present invention can prevent problems associated with, among other things, giving a patient incorrect medication, which can cause a dangerous allergic reaction or drug interaction, and problems associated with blood transfusion reactions. Providing medical personnel with more information generally results in better medical outcomes, lower medical costs, and fewer complications. The present invention can also enable the patient's emergency contact person to be immediately notified of the patient's medical status and location. In some embodiments, the system can be limited to a single hospital or hospital system. In other embodiments, the system can be provided by a central service provider to increase breadth of access.

Embodiments of the invention, however, are not solely limited to use for medical records. Rather, embodiments of the invention can be used whenever information needs to be stored, retrieved, and carried in a convenient manner. The present invention can also be used, for example and not limitation, to store information regarding the bearer's driving or criminal record.

The material described hereinafter as making up the various elements of the present invention are intended to be illustrative and not restrictive. Many suitable materials or technologies that would perform the same or a similar function as the materials and technologies described herein are intended to be embraced within the scope of the invention. Such other materials not described herein can include, but are not limited to, materials that are developed after the time of the development of the invention, for example.

Figure 1A:
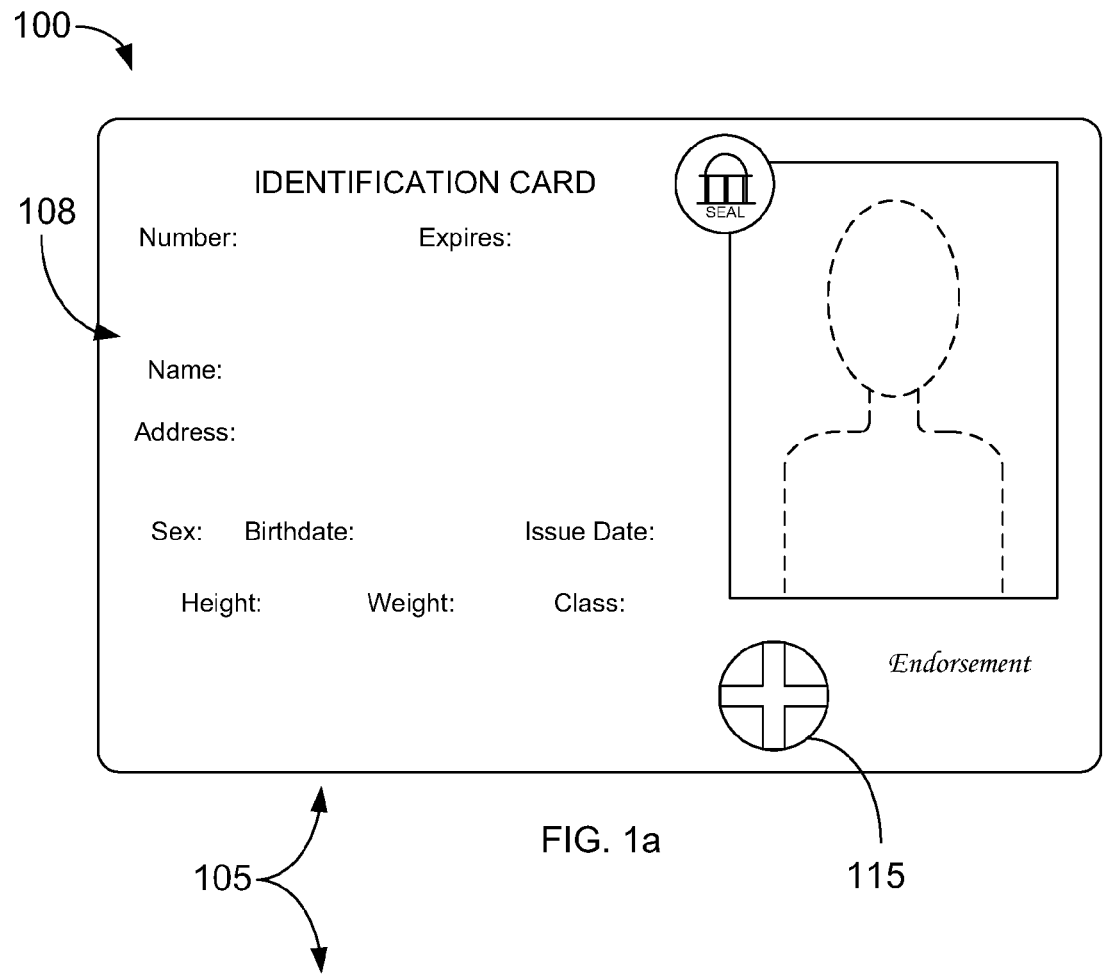
FIG. 1a illustrates a front view of an identification card with a universal personal emergency medical information retrieval system, in accordance with some embodiments of the present invention.
Figure 1B:
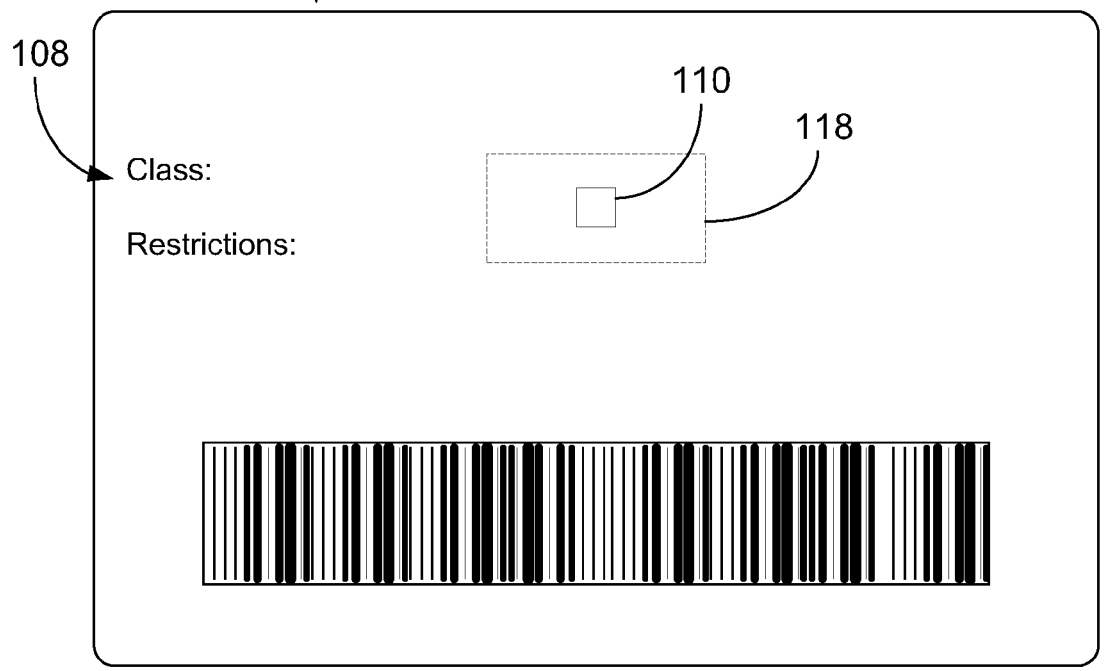
FIG. 1b illustrates a rear view of an identification card with a universal personal emergency medical information retrieval system, in accordance with some embodiments of the present invention.

Referring now in detail to the drawings, wherein like reference numerals represent like parts throughout the several views, FIGS. 1a and 1b depict a system 100 for providing critical medical information to medical personnel utilizing a conventional identification card or driver's license ("ID") 105. The ID 105 depicted is illustrative only and could be any common form of identification such as, for example and not limitation, a state issued ID card, a state issued driver's license, a passport book, a passport card, a library card, or school ID. The ID 105, depending on type, can include various information 108 including, but not limited to, name, address, height, weight, and date of birth. The use of the system 100 in conjunction with existing forms of ID 105 increases the likelihood that patients will have their ID 105, and thus their medical records, with them when needed.

The front of the card, shown in FIG. 1a, can be substantially unmodified, but in some embodiments can include a system identifier 115. The system identifier 115 is shown in FIG. 1a as a cross within a circle, but could be any universally agreed upon symbol. The system identifier 115 could be, for example and not limitation, a stamp, sticker, decal, or medallion. Additionally, the system identifier 115 could be, for example and not limitation, self-adhesive, glued, imprinted, or otherwise securely adhered to the ID 105. The system identifier 115 can preferably be securely attached to the ID 105 in a manner that enables it to be removed without damaging the ID 105.

The system identifier 115 can preferably be distinctive and easily identifiable. This can enable providers to quickly search the patient's wallet and/or belongings, if necessary, to determine if the system 100 is present. In some embodiments, the system identifier 115 can include information regarding the service provider for the system 100 and can include additional information, such as a website or phone number. In some embodiments, the system identifier 115 can include, for example and not limitation, glow-in-the-dark, magnetic, radioactive, or other features to assist medical personnel in its location.

Figure 2:
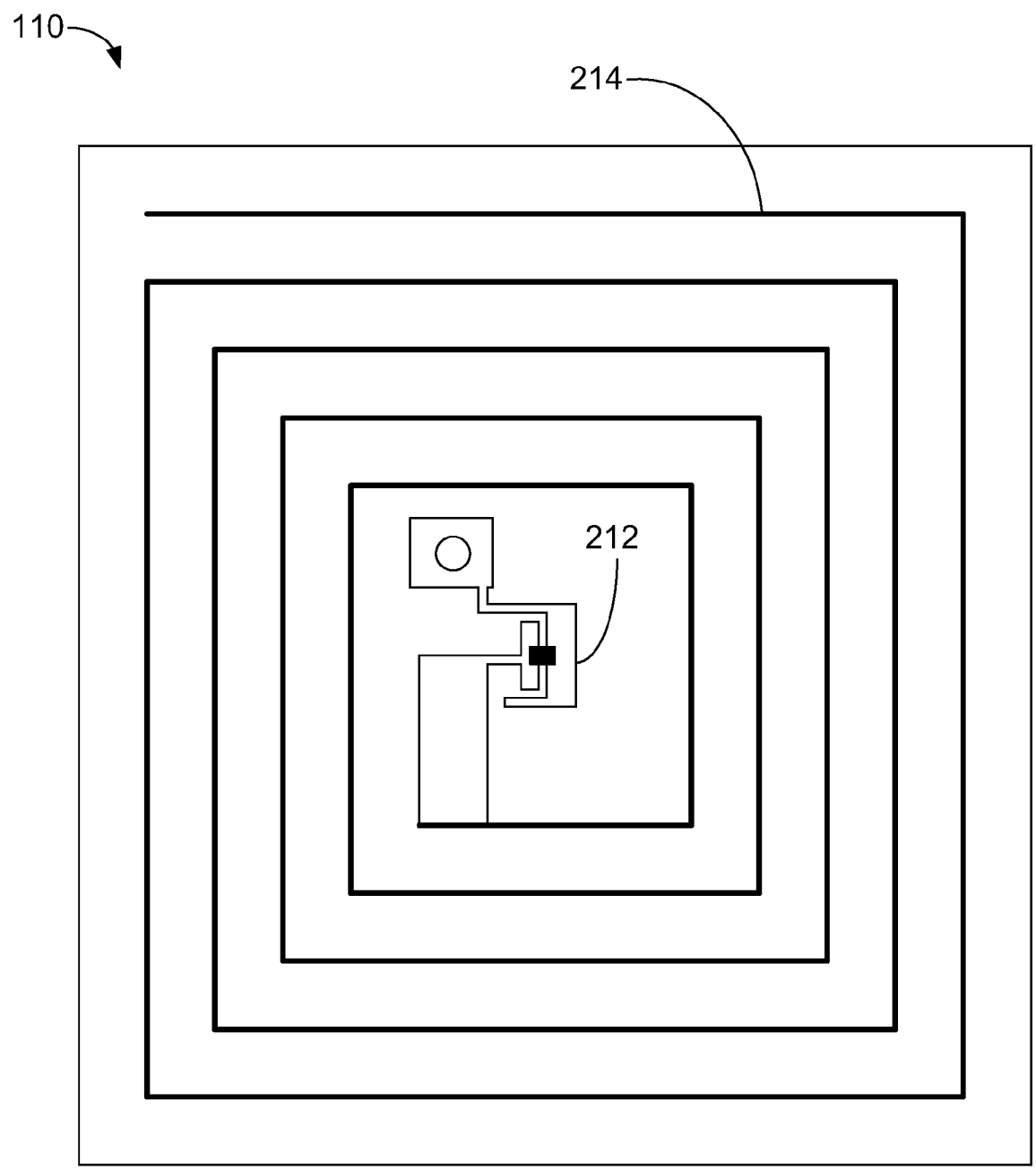
FIG. 2 illustrates a top view of an RFID tag for use with a universal personal emergency medical information retrieval system, in accordance with some embodiments of the present invention.

In some embodiments, shown in FIG. 1b, the system 100 can use a radio frequency identification tag ("RFID") 110 to store critical information. In some embodiments, the RFID 110 can comprise a passive RFID tag. As shown in FIG. 2 passive RFID tags conventionally comprise an integrated circuit 212, for storing and processing information, modulating and demodulating radio-frequency (RF) signals, and other specialized functions; and an antenna 214 for receiving and transmitting the signal. The passive RFID tag is a preferred method for carrying the emergency medical information because it can be small enough that it can easily be affixed to the back of an identification card, like a driver's license, without adding noticeable bulk to the card. On the other hand, it can store significant amounts of information unlike, for example, an ID bracelet. Additionally, RFID scanners are relatively inexpensive, so the cost to a hospital emergency room, emergency clinic, or ambulance provider is not prohibitive.

In the passive configuration, the RFID 110 can be made at a low cost and can be as small as, for example, a grain of salt. Reducing the size of the RFID 110, however, translates to a corresponding decrease in the size of the antenna 214. So, for example, an RFID 110 the size of a grain of salt can have a tiny antenna 214 etched onto a continuous circuit board, but may only be readable at a distance of less than an inch. The size of the RFID 110, therefore, can be chosen based on, among other things, the desired readability distance, data storage capacity, size, weight, and cost.

In some embodiments, the RFID 110 can be attached to the ID 105 using an adhesive such as, for example and not limitation, epoxy, hot glue, or urethane. In a preferred embodiment, the adhesive can enable the RFID 110 to be attached to the ID 105 in a secure manner; yet can enable the RFID 110 to be removed without damaging the RFID 110 or the ID 105. This can enable the RFID 110 to be removed or replaced when necessary, such as when the RFID 110 becomes damaged or a patient's information changes. In some embodiments, a cover 118 can go over the top of the RFID 110 to limit or prevent damage to the RFID 110 from normal wear and tear. In some embodiments, the cover 118 can be a clear, self-adhesive sticker, though other configurations are contemplated.

In other embodiments, the RFID 110 can be built into the ID 105 during manufacture or can be added as part of the issuance process. In other words, the RFID 110 can be embedded in the plastic, or other material, of the ID 105 when it is manufactured, or can be inserted into the ID 105 material when the ID 105 is printed using a suitable device. In other embodiments, the ID 105 can be manufactured with a hole or slot designed to receive the RFID 110. This can enable the RFID 110 to be replaced if necessary without replacing the ID 105. Placing the RFID 110 inside the ID 105 can help protect the RFID 110 from shock and wear during normal use.

In still other embodiments, shown in FIGS. 3a, 3b, and 3c, the system 300 can be used in conjunction with the user's cell phone 305. This can be advantageous for users who carry a cell phone 305 instead of, or more than, they carry an ID 105. This can also enable a user to carry more than one RFID 110, if desired, for the sake of redundancy. In other words, the probability is greater that a user will have an RFID 110 with them, either in a cell phone 305 or an ID 105, at any given time.

The front of the phone, shown in FIG. 3a, can be substantially unmodified, but in some embodiments can include a system identifier 115. The system identifier 115 is shown in FIG. 3a as a cross within a circle, but could be any universally agreed upon symbol. The system identifier 115 could be, for example and not limitation, a stamp, sticker, decal, or medallion. Additionally, the system identifier 115 could be, for example and not limitation, self-adhesive, glued, imprinted, or otherwise securely adhered to the cell phone 305. The system identifier 115 can preferably be securely attached to the cell phone 305 in a manner that enables it to be removed without damage to the cell phone 305.

In some embodiments, such as when the cell phone 305 is a "flip phone," i.e., one that folds to close, the RFID 110 can be attached to a portion of the cell phone 305 that is interior when closed. Mounting the RFID 110 inside the folded portion of the cell phone 305 protects the RFID 110 from wear and damage without having to open the cell phone 305 case or battery cover 310 of for installation. This can prevent problems with damaging the cell phone 305 and/or voiding the cell phone 305 warranty.

In another embodiment, the RFID 110 can be attached to the back of the cell phone 305 using an adhesive such as, for example and not limitation, epoxy, hot glue, or urethane. In a preferred embodiment, the adhesive can enable the RFID 110 to be attached to the cell phone 305 in a secure manner; yet can enable the RFID 110 to be removed without damaging the RFID 110 or the cell phone 305. This can enable the RFID 110 to be replaced when necessary, such as when the RFID 110 becomes damaged or a patient's information changes. In some embodiments, a cover 118 can go over the top of the RFID 110 to limit or prevent damage from normal wear and tear. In some embodiments, the cover 118 can be a clear, self-adhesive sticker, though other configurations are contemplated.

In still other embodiments, the RFID 110 can be placed in the battery compartment 310, or other interior compartment, of the cell phone 305. This can also enable the RFID 110 to be securely held inside the cell phone 305 and can obviate the need for adhesive or a sticker 118. This can enable the RFID 110 to be protected from shock and wear by the case of the cell phone.

In other embodiments, the RFID 110 can be built into the cell phone 305 during manufacture. In other words, the RFID 110 can be embedded into the material of, installed as a component of, or inserted into a suitable location in the cell phone 305 when it is manufactured. In other embodiments, the cell phone 305 can be manufactured with a slot or hole designed to receive the RFID 110. This can enable the RFID 110 to be replaced if necessary without replacing the cell phone 305.

In still other embodiments, the RFID 110 can be attached to, or housed in, a sleeve or carrying case designed to fit the ID 105 or cell phone 305. The sleeve can be, for example and not limitation, a clear plastic sleeve designed to slide over the ID 105 or cell phone 305. This can provide protection not only for the ID 105 or cell phone 305, but for the RFID 110. In other embodiments, the RFID 110 can be attached to, or housed in, a carrying case designed for use with the cell phone 305. In some embodiments, the sleeve or carrying case can further comprise the system identifier 115. This can enable the system 100, 300 to be used in conjunction with an ID 105 or cell phone 305 without modification to the ID 105 or cell phone 305.

In some embodiments, the RFID 110 can comprise data related to the user and the user's medical record. The amount of data stored on the RFID 110 can vary depending on the storage capacity of the RFID 110. In some embodiments, therefore, the RFID 110 can contain only a unique system identification number for the user that can be retrieved by medical personnel using an RFID scanner. Medical personnel can use this system identification number to retrieve the user's medical file from a central service provider. Medical personnel will be required to obtain a unique password and be authenticated before access to medical files is granted by the service provider for privacy and security purposes.

In other embodiments, the RFID 110 can contain a digital picture of the user, the user's system identification number, and the phone number or website of the service provider. In still other embodiments, the RFID 110 can also contain some or all of the user's medical history. The amount of information stored on the RFID 110 is, at present, technology and size limited. As RFID 110 technology advances, however, the amount and quality of information that can be stored on a suitably sized RFID 110 will continue to increase.

In some embodiments, the RFID 110 can comprise a flexible database structure enabling it to be tailored to individual patients. The information stored for a particular patient can be determined by, for example, the patient, the patient in conjunction with their primary care physician, or the patient in conjunction with the service provider. In some embodiments, the user can simply log on to a website using a unique password and enter their medical history and personal information directly to their file. In other embodiments, the user can call a service provider call center and relay their information to a service provider representative. This can benefit users, for example, who do not have internet access or who need assistance for health or other reasons.

The amount of information that needs to be stored in a user's file can vary widely. The elderly, or those with extensive or serious medical problems, for instance, can require a significant amount of information to be stored in the user's file or on the RFID 110. A relatively healthy patient, on the other hand, may only require a minimal amount of information due to their comparatively brief medical history. In some embodiments, information stored on the RFID 110 can include for example and not limitation, the user's system identification number, the service provider's website or phone number, blood type, blood factors, allergies, past and present medications, surgical history, current or chronic medical conditions, emergency contact information, medical insurance provider, account, and group number, and their doctor's names and phone numbers.

In a preferred embodiment, the information on the RFID 110 will be encrypted or password protected for security purposes. In some embodiments, a non-rewriteable RFID 110 can be used to prevent non-qualified or non-approved individuals from changing the medical information on the chip thus assuring the information contained on the RFID 110 is accurate. In some embodiments, the RFID 110 can contain only the user's unique system identification number and will not need to be updated. In other embodiments, the RFID 110 can be rewriteable enabling medical personnel with proper passwords or credentials to modify some or all of the information contained thereon.

In either instance, every time medical personnel access the information on the RFID 110 or the user's file from the service provider, an entry can be made in the user's file. This entry can include, for example and not limitation, the name of the medical personnel that access the file (based on their unique password) and their employer, the time the file was accessed, and which portions of the user's file was accessed. This can create a record of all access to a user's file and can help maintain the security and privacy of the file. These entries can also be useful, for example, when attempting to determine what information medical personnel based their decisions on, i.e., when there is an adverse outcome.

In some embodiments, the user can also access her medical file using a unique password. In some embodiments, the user can, for example and not limitation, add medical or personal information, change emergency contacts, and update her medical records as needed. Each time the user accesses her file, an entry can be made denoting what data was changed or added, and the time the data was changed. These entries can also be useful, for example, when attempting to determine what information medical personnel based their decisions on, when relevant.

In some instances, people are coincidentally (or intentionally) carrying an ID 105 or cell phone 305 that is not theirs. This can happen for various reasons including when one person is wearing clothes that lack pockets, or is not carrying a purse or wallet, and asks another to hold their ID 105 or cell phone 305. It is also common for one person to attempt to receive healthcare using another person's information. This can happen, for example, when one lacks health insurance or due to one's immigration status. Using the information stored on the RFID 110 or stored in the user's file, such as for example, blood type or current medications, to treat the wrong person can be harmful or fatal.

If, for example, the ID 105 is used in conjunction with the system 100 lacks a picture, or if the picture has been tampered with, a backup method of identification can be provided. In some embodiments, therefore, the information stored on the RFID 110 can include a digital picture of the patient. This can enable the medical personnel to identify the owner of the ID 105 or cell phone 305 and ensure that the information stored thereon is properly applied, or ignored, as appropriate. This provides an important safety check to be sure that the system identification number or medical information stored on the RFID 110 belongs to the patient being treated. In an alternative embodiment, such as when the RFID 110 lacks the ability to store digital photographs, the user's digital photograph can be stored by the service provider in the user's file for verification.

In some embodiments, a user may wish to include information for more than one person on their RFID 110. This can be, for example and not limitation, a parent who wishes to store information about themselves and a child. This can be useful when, for example, a parent and child are both in an accident. If the parent is incapacitated, the child may be too young to know relevant medical and personal information. The RFID 110 can be used to retrieve information about both patients. The patients' files will be easily distinguishable by at least their digital photograph and often their date of birth.

Figure 4:
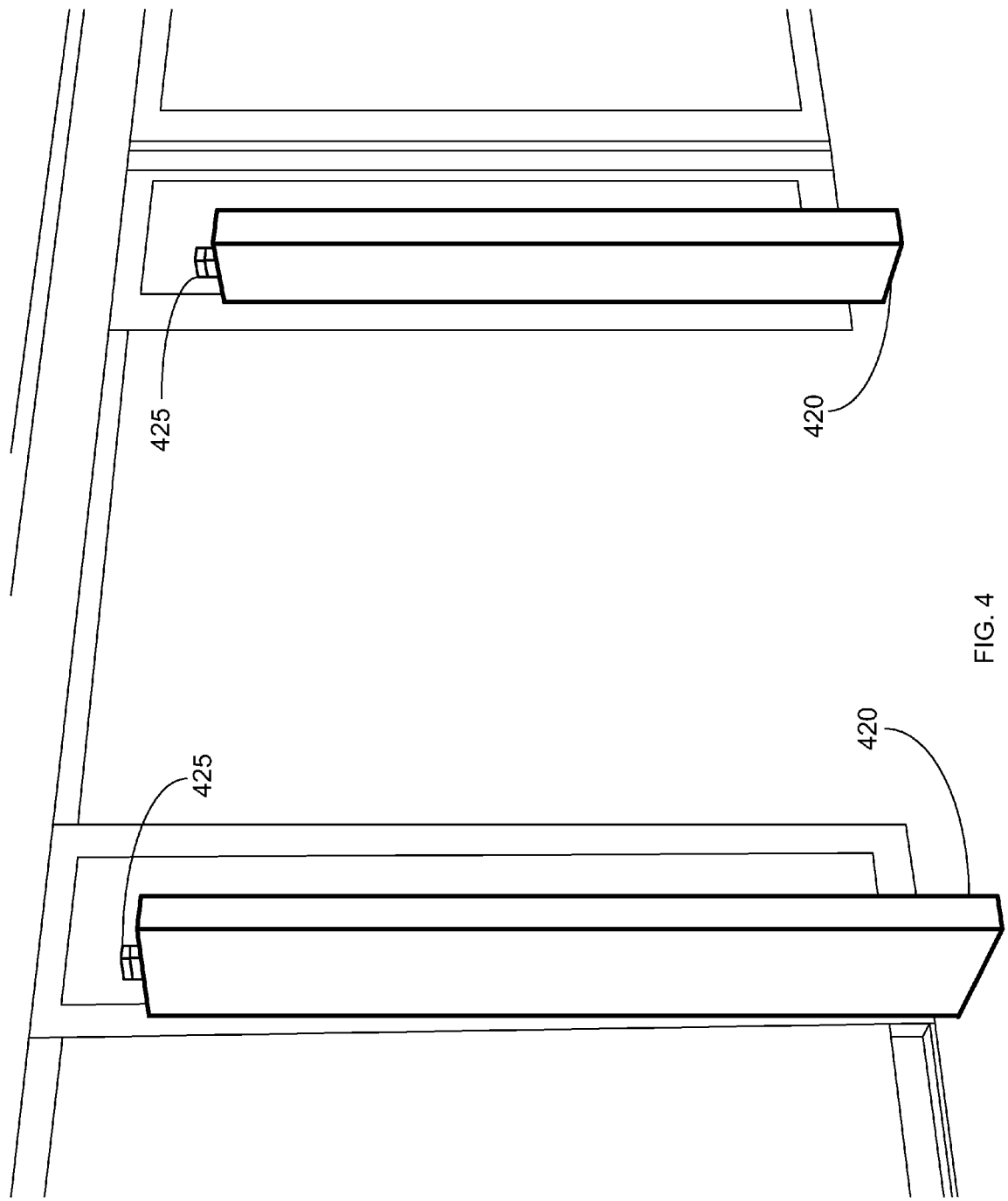
FIG. 4 illustrates a perspective, front view of an RFID portal for use with a universal personal emergency medical information retrieval system, in accordance with some embodiments of the present invention.

In some embodiments, shown in FIG. 4, the RFID 110, and thus the antenna 214, can be sized such that all patients entering a medical facility, such as for example, an emergency room, pass through a portal 420 that scans for readable RFIDs 110. This can enable the medical information for all patients equipped with the system 100, 300 to be retrieved as soon as the patient passes through the portal 420. This obviates the need to locate the user's ID 105 or cell phone 305 and can further expedite information retrieval.

In some embodiments, the portal 420 can be equipped with one or more alerting means 425, such as for example and not limitation, lights, strobes, or speakers, to alert personnel that the system 100, 300 is present on a particular patient. In some embodiments, the portal 420 can serve only to alert medical personnel of the presence of the system. In this configuration, the portal 420 can have the capability to detect the presence of the RFID 110. This can enable the portal 420 to be relatively simple and inexpensive. Upon detecting the presence of the RFID 110, the portal 420 can activate the alerting means 425 to alert medical personnel of the presence of the system.

In other embodiments, the portal 420 can be adapted to read the RFID 110 and can be networked to a computer located, for example and not limitation, at the admitting desk of the hospital or in the hospital's emergency room. The portal 420 can be networked using, for example and not limitation, wired or wireless networking technologies. This can enable the portal 420 to automatically retrieve the user's system identification number and, in turn, retrieve the user's medical file. This can save the step of having to find and scan the user's RFID 110 and can provide admitting personnel and medical personnel with critical information in a timely manner. In still other embodiments, the portal 420 can provide the user's system identification number to the admitting desk computer, which can then automatically access the patient's medical history.

Figure 5:
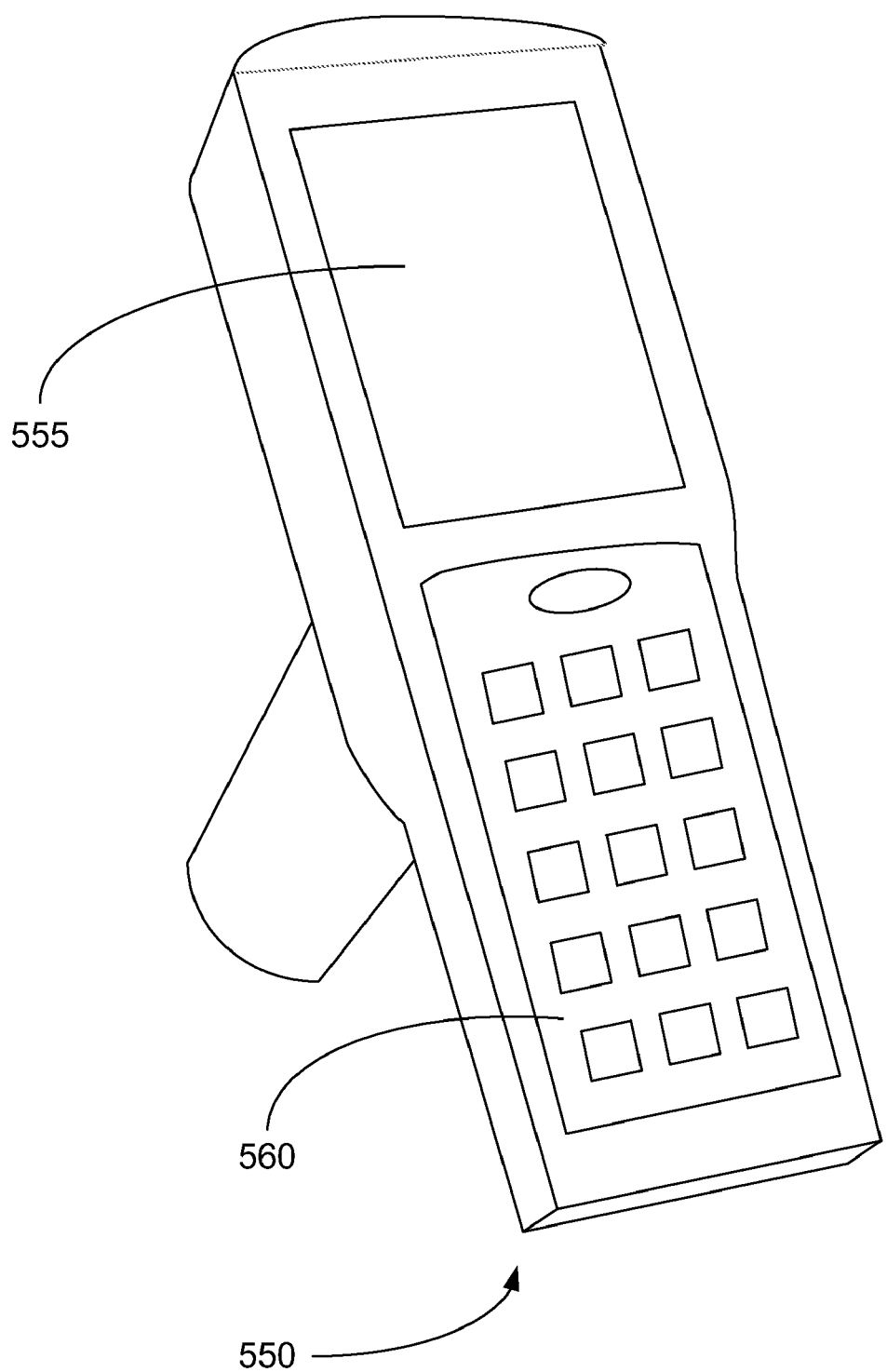
FIG. 5 illustrates a perspective, front view of a handheld RFID scanner for use with a universal personal emergency medical information retrieval system, in accordance with some embodiments of the present invention.

In still other embodiments, medical personnel can be equipped with handheld RFID scanners 550, a generic depiction of which is shown in FIG. 5. The Scanner 550 can be any commercially available scanner 550 such as, for example and not limitation, the Metrologic MS9535 VoyagerBT Handheld Scanner. Handheld scanners are readily available and relatively inexpensive (approximately $200-$400). This can enable medical personnel to quickly retrieve the information stored on the RFID 110.

In some embodiments, the scanner 550 can comprise a monochrome or color screen 555. In some embodiments, the screen 555 can display the information contained on the RFID 110 on a graphical user interface (GUI). In other embodiments, the screen 555 can display the digital picture of the patient stored on the RFID 110. As mentioned, above this can help prevent misapplication of the information stored on the RFID 110. In some embodiments, the scanner 550 can further comprise a keyboard 560 to enable medical personnel to, for example and not limitation, scroll through the GUI or make notes. In some embodiments, the scanner 550 can be used as the primary method for retrieving the information stored on the RFID 110. In some embodiments, medical personnel can then simply transfer the relevant information from the RFID 110 to the patient's chart for future reference.

Figure 6:
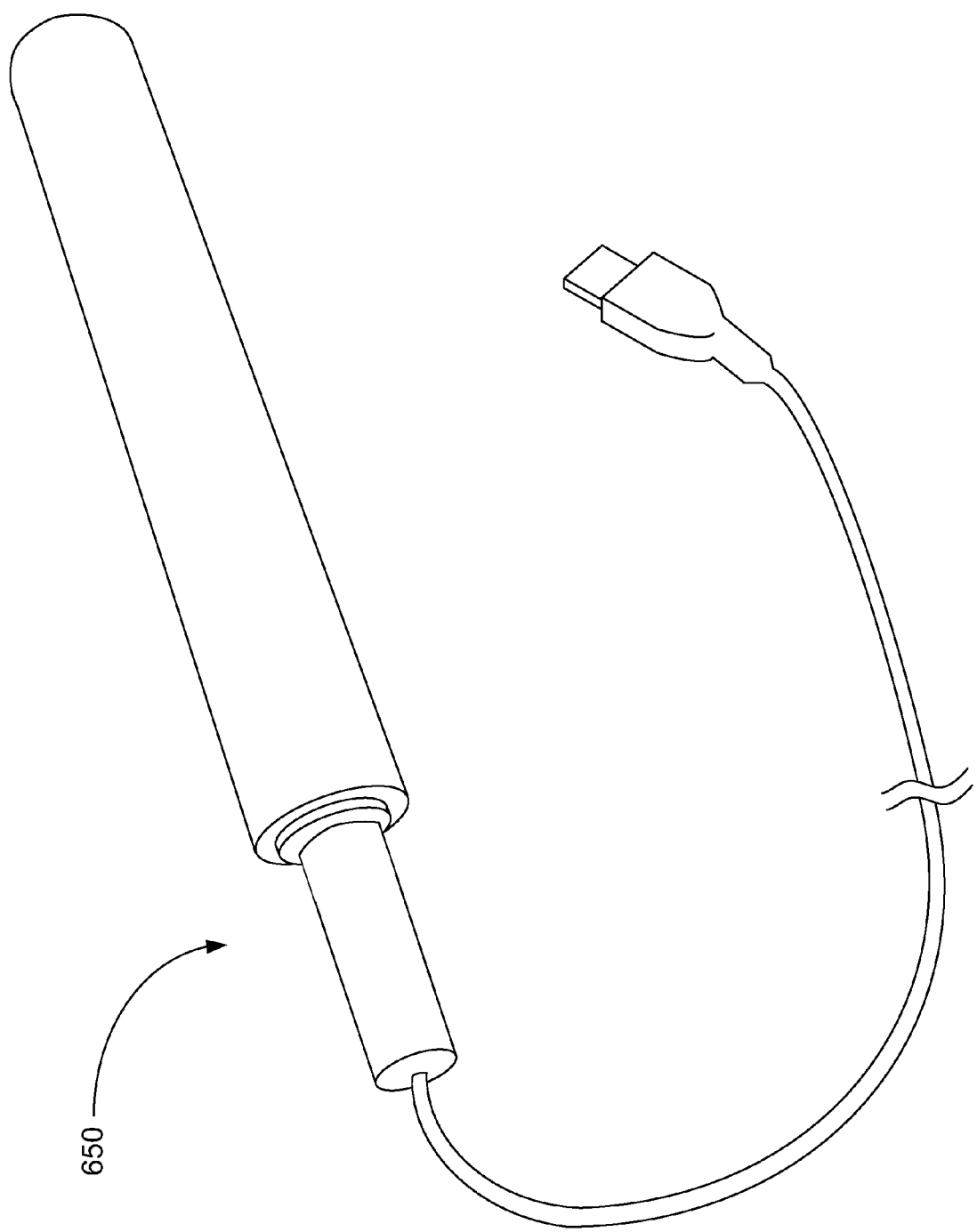
FIG. 6 illustrates a perspective, front view of a handheld wand-type RFID scanner for use with a universal personal emergency medical information retrieval system, in accordance with some embodiments of the present invention.

In still other embodiments, shown in FIG. 6, the system 100 can further comprise a wand-type scanner 650. In some embodiments, the scanner 650 can be linked directly to a computer or network located in the hospital. This can enable medical personnel to scan the user when they arrive and read the information on the RFID 110 directly into the computer system at the hospital. In some embodiments, the wand-type scanner 650 can provide a lower cost, more rugged alternative to the handheld scanner 550 and can increase security by directly, as opposed to wirelessly, interfacing with hospital systems.

Figure 7:
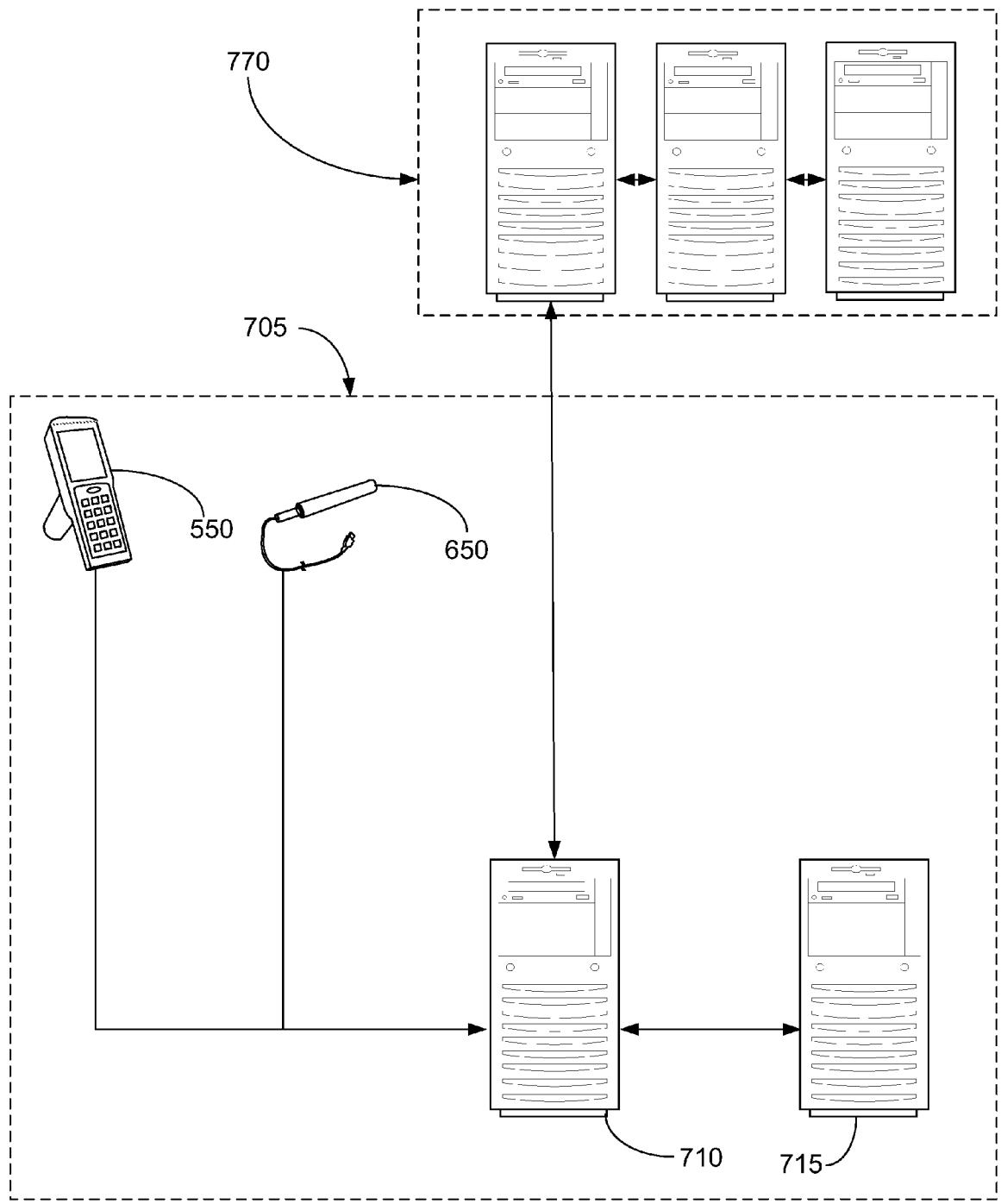
FIG. 7 illustrates a network diagram of a local database and a central database for use with a universal personal emergency medical information retrieval system, in accordance with some embodiments of the present invention.

In some embodiments, shown in FIG. 7, the scanner 550, 650 can be networked with a computer network 705 installed in a hospital. In some embodiments, this network can include a computer located at the admitting desk 710. In other embodiments, the network can include a database on locally maintained and operated servers 715 to store complete medical records for patients. The scanner 550, 650 and computers 710, 715 can be networked with a wired network, for example, or by wireless or cellular means.

In some embodiments, the scanner 550, 650 can be connected via wireless or cellular means to the computers 710, 715 at the hospital. This can enable transfer of the information stored on the RFID 110 from an ambulance to the receiving hospital while en route. In this scenario, the receiving hospital can have the information from the RFID 110 when the patient arrives in the emergency room and can also have extra time to retrieve additional information from a local server 715, if applicable.

The network can enable the hospital to access patient medical information using an internal, centralized database on a server 715 from anywhere in the hospital. If a former patient is admitted to the hospital, his medical records can be retrieved automatically upon scanning his RFID 110. In some embodiments, the scanner 550, 650 can have the ability to retrieve information from the central local server 715 using, for example, a cellular or wireless network connection.

In some embodiments, also shown in FIG. 7, the system 100, 300 can further comprise a central database storage facility 770. The central database storage facility 770 can facilitate storage of additional medical information for each patient. In some embodiments, a patient's complete medical history can be stored and maintained on the central database storage facility 770. In some embodiments, the RFID 110 can direct medical personnel to a website, phone number, or other contact information to quickly access the portion of the patient's medical history not stored on the RFID 110. This can enable medical personnel in non-emergent situations to make decisions based on still more complete information.

In some embodiments, the central database storage facility 770 can be provided by a remote service provider. This can enable patient medical files and records to be stored using a database hosting site, such as www.fastservers.net, rather than operating physical servers at the owners' site. This greatly reduces the possibility of data unavailability due to a crashed server or internet connection loss, because database host sites use redundant servers and connections. This can also enable multiple hospitals to access a patient's records in a centralized manner.

So, for example, medical personnel arrive at the scene of an accident to find a single car accident and the patient unconscious. The medical personnel can first assess the situation and attend to any immediate needs such as, for example, stemming blood loss or stabilizing injuries. The medical personnel can then look in the patient's wallet or purse for their ID 105 or cell phone 305. In some embodiments, the medical personnel can check for a system identifier 115 disposed on the ID 105 or cell phone 305. If the system identifier 115 is present, the medical personnel are alerted to the presence of the system 100, 300. In other embodiments, the medical personnel can simply scan the patient as a matter of course to detect the presence of the system 100, 300. In other embodiments, the RFID 110 will be readable at sufficient distance that medical personnel merely need to pass the scanner 550, 650 over the patients handbag or wallet and the RFID 110 will be read automatically.

In some embodiments, medical personnel will be equipped with a small handheld wand-type scanner 650 connected directly to the central or admitting computer for the hospital. In some embodiments, the scanner 650 can read the users system identification number and automatically retrieve the user's medical information from the service provider. This can expedite treatment and can facilitate electronic, or "chartless," medical record keeping. When the user's medical record is retrieved, the information contained therein will automatically be included in the user's electronic chart. In some embodiments, the hospital may wish to generate a paper copy for archival or back-up purposes that can be generated automatically if desired.

In some embodiments, the medical personnel can be equipped with a handheld scanner 550, 650 to read the information on the RFID 110. The display 555 on the scanner can display the information stored on the RFID 110 to assist the medical personnel in making appropriate treatment decisions. In some embodiments, the medical personnel will transfer the information from the scanner 550, 650 to the patient's chart for future reference. In other embodiments, the scanner 550, 650 can be linked, for example, using a wireless or cellular connection, to the receiving hospital. This can enable the receiving hospital to receive the information on the RFID 110 prior to the patient's arrival. In other embodiments, the receiving hospital can retrieve additional information from the central database 770 prior to the patient's arrival.

In other embodiments, for example, the patient can be brought into the emergency room of the receiving hospital by, for example, medical personnel, a neighbor, or a parent. In some embodiments, the receiving hospital can be equipped with an RFID scanning portal 420. This can enable all patients entering, for example, the emergency room doors, to be scanned for the system 100, 300. In some embodiments, the portal 420 can be equipped with an alerting means 425 to alert Medical personnel at the receiving hospital to the presence of the system 100.

In some embodiments, the portal 420 can be networked with, for example and not limitation, the admitting desk at the receiving hospital and can scan and retrieve the information stored on the RFID 110. This can enable, for example, the admitting nurse to relay critical information to the Medical personnel and to add relevant information to the patient's admitting chart. In some embodiments, this can also enable the admitting nurse to access the central database 770 to retrieve additional information, if applicable. In some embodiments, the portal 420 can automatically initiate retrieval of the patient's full medical record from the central database 770.

In other embodiments, the portal 420 can have only an alerting function and the Medical personnel at the admitting hospital can be equipped with handheld scanners 550, 650. In some embodiments, the Medical personnel can look in the patient's wallet or purse for an ID 105 or cell phone 305 with a system identifier 115. Upon finding the user's ID 105 with a system identifier 115, the medical personnel can scan the ID 105 or cell phone 305 with the handheld scanner 550, 650 to retrieve the information on the RFID 110. In other embodiments, the range over which the RFID 110 can be scanned can be such that medical personnel can simply pass the scanner 550, 650 over the user to read the RFID 110.

In some embodiments, the medical personnel can then compare the photo displayed on the handheld scanner 550 to verify the patient's identity. In some embodiments, the medical personnel can then transfer the information stored on the RFID 110 to the patient's admitting chart manually and/or disseminate relevant information to medical personnel working on the patient. In other embodiments, the scanner 550, 650 can be connected, for example and not limitation, wirelessly to a computer network in the admitting hospital to enable admitting personnel to access the information on the RFID 110. This can facilitate electronic charting or can enable an admitting chart to be produced automatically by computer to minimize time and effort spent writing information manually. In some embodiments, the system 100, 300 can automatically access the central database 770 and can add the information stored therein to the chart.

Because the RFID 110 can be contained on a universally accepted identification card 105 such as a driver's license or can be used in conjunction with a cell phone 305, it is likely the patient will carry this information when away from home. The patient does not have to remember to put on jewelry or carry their medical information with them whenever they leave the house. Additionally, responding medical personnel can scan the patient or, if necessary, quickly look through a person's belongings to locate this information. Using an RFID 110 with a suitable range, along with the use of the system identifier 115 on the front of the identification card 105 or cell phone 305, will immediately alert medical personnel to the presence of the system 100, 300, thus saving time that can be critical in an emergency setting.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, materials, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A universal personal emergency medical information retrieval system comprising:
a carrying element;
a radio frequency identification (RFID) tag-affixed to the carrying element, the RFID tag storing a unique system identification number; and
a portal sized such that a patient can pass through the portal, the portal reading the RFID tag and retrieving the unique system identification number from the tag, and the portal alerting medical personnel that an RFID tag has passed through the portal; wherein the portal is in communication with a computer system that: receives the unique system identification number from the portal; asks a user to supply a password; and provides access to medical information from to central database if the password is correct.

2. The universal personal emergency medical information retrieval system of claim 1, wherein the carrying element is a form of identification.

3. The universal personal emergency medical information retrieval system of claim 1, wherein the carrying element is a cell phone.

4. The universal personal emergency medical information retrieval system of claim 1, wherein the RFID tag comprises a passive RFID tag.

5. The universal personal emergency medical information retrieval system of claim 1, wherein the information stored on the RFID tag includes a digital picture of the patient to confirm the identity of the patient.

6. The universal personal emergency medical information retrieval system of claim 1, further comprising an RFID tag protector, disposed in an overlying manner to the RFID tag, to provide protection for the RFID tag.

7. The universal personal emergency medical information retrieval system of claim 1, wherein the portal is in communication with a computer system that:
receives the unique system identification number from the portal;
asks a user to supply a password; and
provides access to medical information if the password is correct.

8. The universal personal emergency medical information retrieval system of claim 1, wherein the RFID is detachably affixed to the carrying element.

9. The universal personal emergency medical information retrieval system of claim 1, wherein the RFID is permanently affixed to the carrying element.

10. A universal personal emergency medical information retrieval system comprising:
a radio frequency identification (RFID) tag carried by a cell phone, the RFID tag storing a unique system identification number;
a portal sized such that a patient can pass through the portal, the portal reading the RFID tag and retrieving the unique system identification number from the tag, the portal located proximate to an entrance of a room of medical facility, the portal further adapted to alert medical personnel that an RFID tag has passed through the portal;
wherein the portal is in communication with a computer system that:
receives the unique system identification number from the portal;
asks a user to supply a password; and provides access to medical information from a central database if the password is correct.

11. The universal personal emergency medical information retrieval system of claim 10, wherein the central database is maintained by a central database hosting website.

12. The universal personal emergency medical information retrieval system of claim 10, wherein the central database is maintained locally in one of a hospital or a hospital network.

13. The universal personal emergency medical information retrieval system of claim 10, wherein the RFID tag stores a plurality of unique system identification numbers.

14. The universal personal emergency medical information retrieval system of claim 10, wherein the unique system identification number can only be written to the RFID tag one time.

15. In a system comprising a carrying element and an RFID tag, a method for providing universal personal emergency medical information comprising:
  writing a user's unique system identification number to the RFID tag using an RFID tag writer;
  detachably affixing the RFID tag to the carrying element;
  a patient possessing the carrying element and passing through a portal, the portal reading the RFID tag and retrieving the unique system identification number from the tag, the portal located proximate to an entrance of a room of a medical facility;
  alerting medical personnel that an RFID tag has passed through the portal;
  the portal communicating the unique system identification number to a computer;
  the computer requesting a user to supply a password; and
  the computer providing access to medical information if the password is correct.

16. The method of claim 15, further comprising:
  detachably affixing an RFID tag protector to the carrying element in an overlying manner to the RFID tag to protect the RFID tag.

17. The method of claim 15, wherein the unique system identification number can only be written to the RFID tag one time.

18. The method of claim 15, wherein the unique system identification number is written to the RFID tag using encryption, password protection, or both.

* * * * *